(12) United States Patent
Vigil (10) Patent No.: US 10,207,036 B2
(45) Date of Patent: Feb. 19, 2019

(54) APPARATUS AND METHOD FOR SECURING AND UTILIZING BREAST PUMPS USING A PERSON'S LEGS

(71) Applicant: Anthony Andrew Vigil, Federal Heights, CO (US)

(72) Inventor: Anthony Andrew Vigil, Federal Heights, CO (US)

( * ) Notice: Subject to any disclaimer, the term of this patent is extended or adjusted under 35 U.S.C. 154(b) by 449 days.

(21) Appl. No.: 14/825,620

(22) Filed: Aug. 13, 2015

(65) Prior Publication Data

US 2017/0043072 A1 Feb. 16, 2017

(51) Int. Cl.
*A61M 1/06* (2006.01)

(52) U.S. Cl.
CPC ....... *A61M 1/062* (2014.02); *A61M 2209/088* (2013.01)

(58) Field of Classification Search
CPC ... A61M 2209/082; A41D 1/205; A41F 1/006
See application file for complete search history.

(56) References Cited

U.S. PATENT DOCUMENTS

| 3,765,421 | A | * | 10/1973 | Poprik | A61M 25/02 128/DIG. 26 |
| 4,671,787 | A | * | 6/1987 | Widman | A61M 25/02 128/DIG. 15 |
| 5,897,519 | A | * | 4/1999 | Shesol | A61M 25/02 602/75 |

* cited by examiner

*Primary Examiner* — Bradley J Osinski
(74) *Attorney, Agent, or Firm* — Dorsey & Whitney LLP (57) ABSTRACT

The various embodiments disclosed relate to straps that attach to manual breast pumps to allow the user to pump breast milk with leg power rather than by hand. One of two straps is wrapped around each of a user's thighs. Both straps have fasteners to enable the straps to be securely wrapped around the thigh. The straps are then connected to a manual breast pump. The breast pump can be connected to the manual breast pump by adding fasteners to the breast pump, or by threading the breast pump hoses through the pump connector. After the breast pump has been connected to the pump connectors, the user places the breast cup on their breasts. The user then begins pumping the manual pump by repeatedly moving their legs in an outward and inward motion.

20 Claims, 5 Drawing Sheets

APPARATUS AND METHOD FOR SECURING AND UTILIZING BREAST PUMPS USING A PERSON'S LEGS

INVENTIVE FIELD

The various embodiments described herein generally relate to apparatus and methods for securing and utilizing breast pumps using a person's legs, such as the person's opposing thighs. In at least one embodiment, the apparatus used for securing and utilizing the breast pump may also be used to store such breast pump and related components for transport.

SUMMARY

The present disclosure relates to methods and apparatuses for pumping breast milk. Breast pumps operate under human power or under electrical power. Regardless of the means of power used to operate the pump, a major problem associated with pumping breast milk is finding a private, hygienic location to pump breast milk. Bathrooms, while private, are not ideal locations to pump breast milk because of hygiene issues. Additionally, breast pumps powered manually require tiring physical exertion by the user. Some breast pumps solved physical exertion issues with pumps powered by leg power. However, leg powered pumps require the pumping apparatus to be placed on the ground. If the most convenient location to pump breast milk is a bathroom, leg powered pumping apparatuses placed on the ground present hygiene issues. The thigh powered breast pumps solves these issues by providing a less strenuous method for powering a breast pump and preventing the pump from touching the ground during operation.

BRIEF DESCRIPTION OF THE DRAWING FIGURES

To further clarify the above and other advantages and features of the various embodiments described hereinafter, a more particular description of at least one of such embodiments will be rendered by reference to specific implementations thereof which are illustrated in the appended drawings. It is to be appreciated that these drawings depict only one or more embodiments and are therefore not to be considered to be limiting the scope of any embodiment(s). The various embodiments will be described and explained with additional specificity and detail through the use of the accompanying drawings in which.

DETAILED DESCRIPTION

The various embodiments of the present disclosure relate to methods and apparatuses for securing and facilitating the hands-free operation of a pump, such as a breast pump, using a person's thighs. Pumps, including breast pumps, commonly operate under either human power or under electrical power. Regardless of the means of power used to operate the pump, a major problem associated with the operation of pumps is the securing and operation of the pump while the pump is in use. Often a pump might be secured by placing it on a floor or other surface and operated using one's hands, feet or otherwise. The securing and/or use of such a pump in such a conventional manner is commonly undesirable for a variety of reasons including, but not limited to, hygiene, ease of use, a person's stamina (in the case of a manually activated foot pump), dexterity (for example, in the case of persons with one or more physical impairments which may prevent or diminish the usefulness of a floor or similar surface secured and/or activated pump), proximity of the pump to the breast, requirement of a user to use their hands to operate the pump, and other reasons. Accordingly, the various embodiments described herein disclose methods and apparatuses for securing and/or activating breast pumps which overcome the before mentioned concerns.

In accordance with at least one embodiment of the present disclosure, methods and apparatuses for securing and/or activating a thigh powered breast pump are described. Such embodiments may include a manual breast pump which is secured and/or activated (in the case of manually activated pumps) using one or more straps secured to a person's opposing thighs. When a manually powered pump is used, in accordance with at least one embodiment, a user thereof may activate the pump by moving her thighs inward and outward, towards and away from their opposing thigh, in a clamshell or pincer type movement. In at least one embodiment, the straps utilized to secure and/or activate the pump may be secured to the person's thigh using straps that attach around the thigh with hook and loop fasteners, such as those commonly referred to as being of a VELCRO™ type. In at least one embodiment, snaps, buttons, zippers, strings and other known fasteners and fastening techniques may be used in addition to and/or as an alternative to hook and loop type fasteners. In at least one embodiment, the straps may include padding on one or more sides of the strap. Such padding may be, for example, provided in a pocket internal to one or more of the straps, in a pocket external to the strap, in both, external to the strap, or otherwise. Such padding may be, for example, removable, non-removable, reusable, single use, washable, non-washable, disposable, recyclable, or a combination of any of the foregoing. When such padding is used, it is to be appreciated the padding may increase the perceived comfort of the user of such straps, when such straps are secured to such person's thigh(s) or other appendages.

In at least one embodiment, one or more of the straps may include multiple straps which may be configured to form a lesser number of straps, such as a single strap for in use while the user is securing and/or activating the pump using their thighs and other straps for use in containing, protecting, transporting a breast pump and related accessories (such as a suction cup, receptacles, tubing, and the like).

In at least one embodiment, the straps may be configurable into a configuration which facilitates the carrying of a breast pump and related accessories. More specifically, when not in use and for at least one embodiment, the straps may be configured to unfold from a single or greater number of strap configurations into a configuration that functions as a carrying case and/or compartment. Such carrying case and/or compartment may be configured to store some or all of the equipment associated with the intended use of the breast pump. When configured as a storage container and/or transport container, the straps may be configured to also function as a climate controlled container, for example, by providing pockets for the storage of cooling mediums, such as ice, frozen gel packs or the like.

Figure 1:
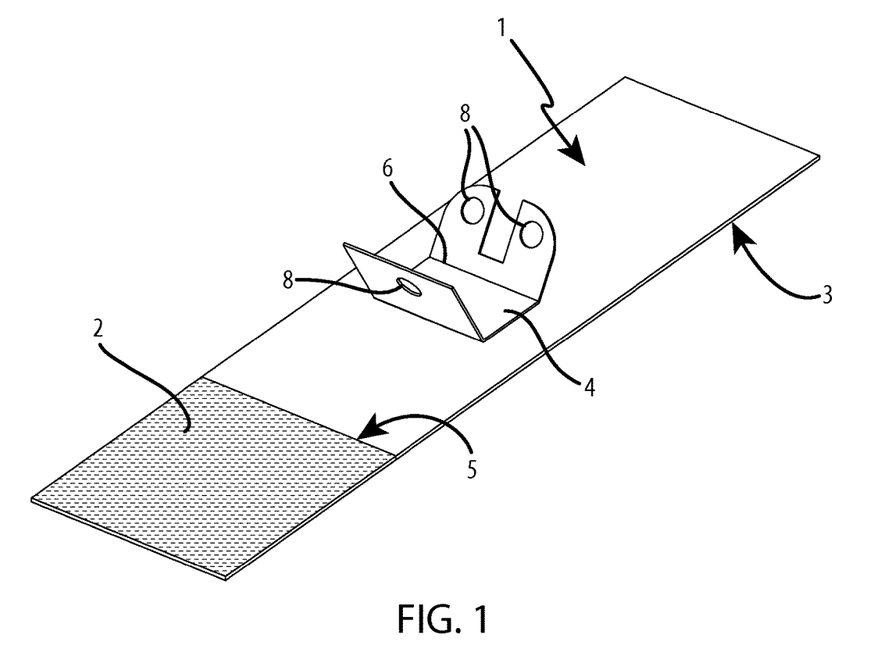
FIG. 1 depicts a single strap that connects to a pump and wraps around the thigh of a user in accordance with at least one embodiment described herein.

FIG. 1 is a diagram illustrating a single strap that includes one or more pump connectors that can be connected to a breast pump and secured to a user's thighs by the wrapping of such a strap around each of a user's opposing thighs in accordance with at least one embodiment disclosed herein. It is to be appreciated that the breast pump may be powered or manually operated. The connection to a breast pump may enable users of the straps to connect to multiple brands for manual breast pump.

Figure 7:
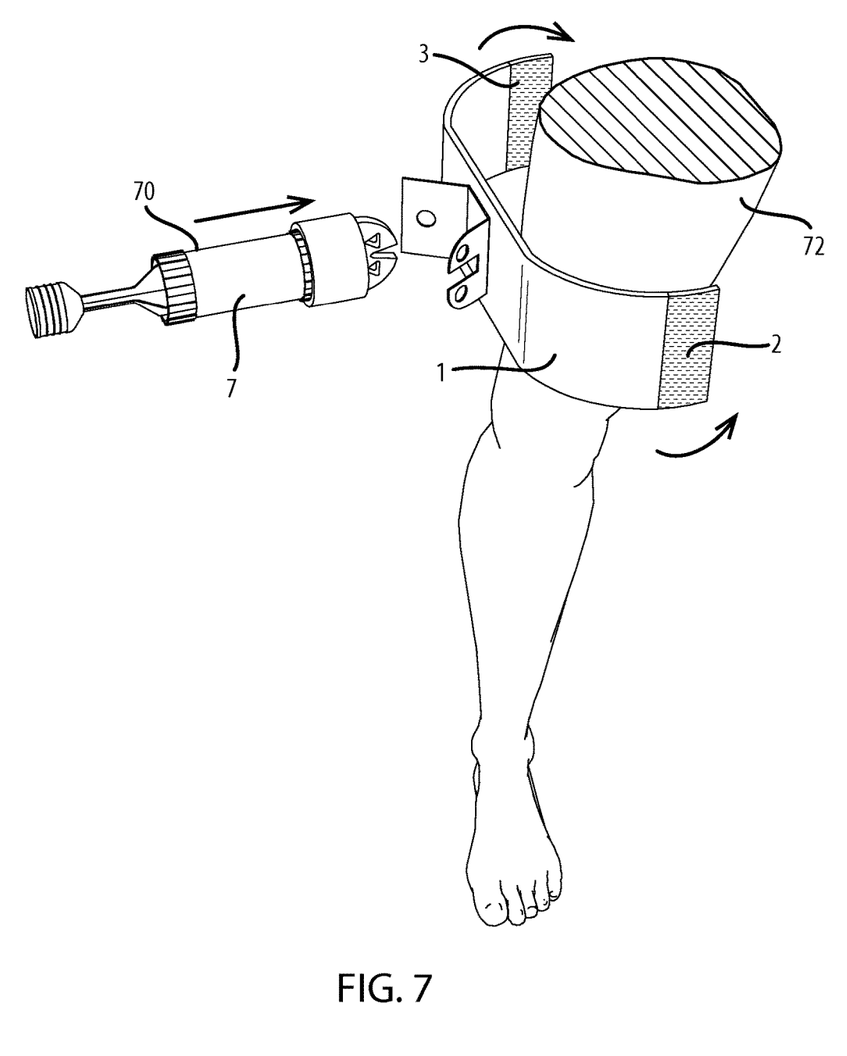
FIG. 7 depicts a fastening of a breast pump to a strap and a strap to a person's thigh in accordance with at least one embodiment described herein.

As illustrated in FIGS. 1 and 7, at least one single strap 1 is utilized to secure a pump 70 (not shown in FIG. 1) to each of a person's thighs 72 (not shown in FIG. 1). The strap 1 may be made of any material desired including, but not limited to, polypropylene, flat nylon, polyester, ribbon, seatbelt webbing, cotton, wool, elastic webbing, natural and/or non-natural fibers and/or other materials and/or compositions of materials. As shown in FIGS. 1 and 7, the strap 1 may include one or more fasteners 2 and 3. In at least one embodiment, fasteners 2 and 3 are opposing hook and loop type fasteners. The hook portion and the opposing loop portion may be configured on a front side (the front side being commonly intended to not contact the user's thigh) or a back side (the side of the strap which faces the user's thigh) of the strap 1. In at least one embodiment, the hook and loop fasteners are 11.5 inches in length from the respective and opposing ends of the strap. In at least one other embodiment, the hook and loop type fasteners may extend over some or a portion of the opposing ends of strap 1, for example, as strips of material arranged longitudinally or perpendicularly to the length of strap 1. Likewise, it is to be appreciated that the hook and loop portions may be configured on either the top and/or the bottom side of the strap, provided the hook portion opposes the loop portion when configured for the intended use of affixing a pump to a woman's thigh or as a storage/carrying case. Further, the fasteners may be attached to the strap 1 with stitching 5, glue, rivets, or otherwise affixed and/or integrated into a portion of the strap itself using known techniques.

Other types of fasteners and fastening mechanisms may be utilized separately, in place of or in combination with hook and loop type fasteners. Examples of other types of fasteners include, but are not limited to, buttons, ties, zippers, adhesive components and others. As shown, the fasteners 2 and 3 are located on opposite ends and on opposite sides of the strap 1 such that the fasteners can connect to each other when wrapped around a user's thigh. In at least one embodiment, strap 1 is 2 inches in width, 35 inches in length and 3 inches in thickness. It is to be appreciated, however, that the strap may be configured at different lengths, widths and/or thicknesses and fasteners may be variously situated along the strap and as desired for any given embodiment. For example, when snaps are used as the fasteners, the snaps corresponding male and female components may be variously placed, and in at least one embodiment evenly spaced, along the length of the strap, for example, from a first end of the strap to 11.5 inches from a distal end of the strap.

The strap 1 is configured to include a pump connector 4. In the embodiments shown in FIGS. 1 and 7, pump connector 4 is centered and located in the middle of the strap 1, in both a horizontal and longitudinal direction. It is to be appreciated, however, the pump connector 4 may be located at any position along the strap 1, including at positions proximate to either end of the strap and/or off-center in either and/or both of the horizontal and longitudinal directions. Further, one or more pump connectors may be positioned on a strap in accordance with any particular and/or desired implementation of one or more of the disclosed embodiments.

In at least one embodiment, pump connector 4 may be made of the same material as strap 1. In other embodiments, pump connector 4 may be made of different materials than the strap. For example, pump connector 4 may be made of and/or include one or more materials that are more durable than the strap. The use of such a more durable material may be used to provide a surface area over which any forces imparted onto a user's thigh during use of the pump is distributed over a greater surface area of such user's thigh, thereby decreasing, minimizing and/or preventing the occurrence of contusions or similar skin ailments arising from use of the one or more embodiments disclosed herein. An example of such materials for use as the pump connector may include an aluminum, steel, carbon or otherwise backing plate that is permanently and/or removable encased in a secondary material, such as a cloth, polyester or otherwise that is used to secure the pump connector 4 to the strap 1 permanently and/or temporarily such as when in use.

In at least one embodiment, the pump connector may be attached to the strap with stitching 6. It is to be appreciated, however, that the pump connector can be attached to the strap permanently or temporarily. In at least one embodiment, pump connector 4 may be attached using the before mentioned hook and loop fasteners. In other embodiments, snaps, buttons, ties, zippers, glue or otherwise may be used to permanently or temporarily attach the pump connector 4 to the strap 1.

The pump connector may be configured to be compatible with, and configured to secure, any type of pump, such as a breast pump. The breast pump may be operated automatically, manually or a combination thereof (e.g., a manually activated but power assisted pump). Desirably, the breast pump has size, weight and compressive characteristics suitable for the intended operation thereof, while also being compatible with one or more of the disclosed embodiments. In at least one embodiment, strap 1 and pump connector 4 may be configured to be used with specific model(s) of breast pump(s). In other embodiments, strap 1 and pump connector 4 may be universal or of a new universal design and are suitably configured to facilitate the secure operation of such pumps using a person's thighs.

As shown in FIG. 7, in the case of use of a manual pump 7, the pump connector 4 may be configured to attach to such a pump in a variety of ways. The pump connector may include fasteners that attach to the manual pump. As illustrated in FIG. 1, the pump connector 4 may include one or more openings, such as holes 8, into which an opposing member for a given pump may be inserted. Other forms and/or orientations of openings may be utilized including, but not limited to, square slots, v-shaped slots or otherwise. As is commonly known and appreciated, manually and automatically operated breast pumps commonly have various hoses that connect to the pump apparatus. Hoses connect to the breast cups to provide suction to the breasts. Hoses are removable in order to enable the user to wash and reuse the hoses. In at least one embodiment, such hoses may be threaded through the holes 8 in the pump connector 4. The hoses provide a connection to the manual pump enabling the user to power the pump with their thighs while securing the pump to such thighs with the respective straps 1.

In at least one embodiment, a breast pump may be connected, via a pump connector 4, to a strap by the use of one or more fasteners. The fasteners may be of any type and/or configuration, including but not limited to, bolts and nuts, toggle bolts, fasteners, pins, carabineers, safety type pins, or otherwise. In at least one embodiment, the pump connector 4 may be integrated with and/or attached to the pump prior to attachment of the pump connector 4 to the straps 1.

In at least one embodiment configured for use with a manual pump, a user utilizes two straps illustrated in FIG. 1. The user wraps one of two needed straps around each of the user's thighs. As discussed above, one or more strap fasteners secure a strap around each of the user's thighs. The user may adjust the length of the straps by adjusting the point of attachment of, for example, the hook and loop fasteners. The user threads the manual pump hoses through the holes 8 in the pump connector 4 and inserts the hoses into the manual breast pump. The user places the breast cup on their breasts. The user repetitively moves her thighs in an outward and inward motion to power the manual pump and impart suction to the breast cups.

Figure 2:
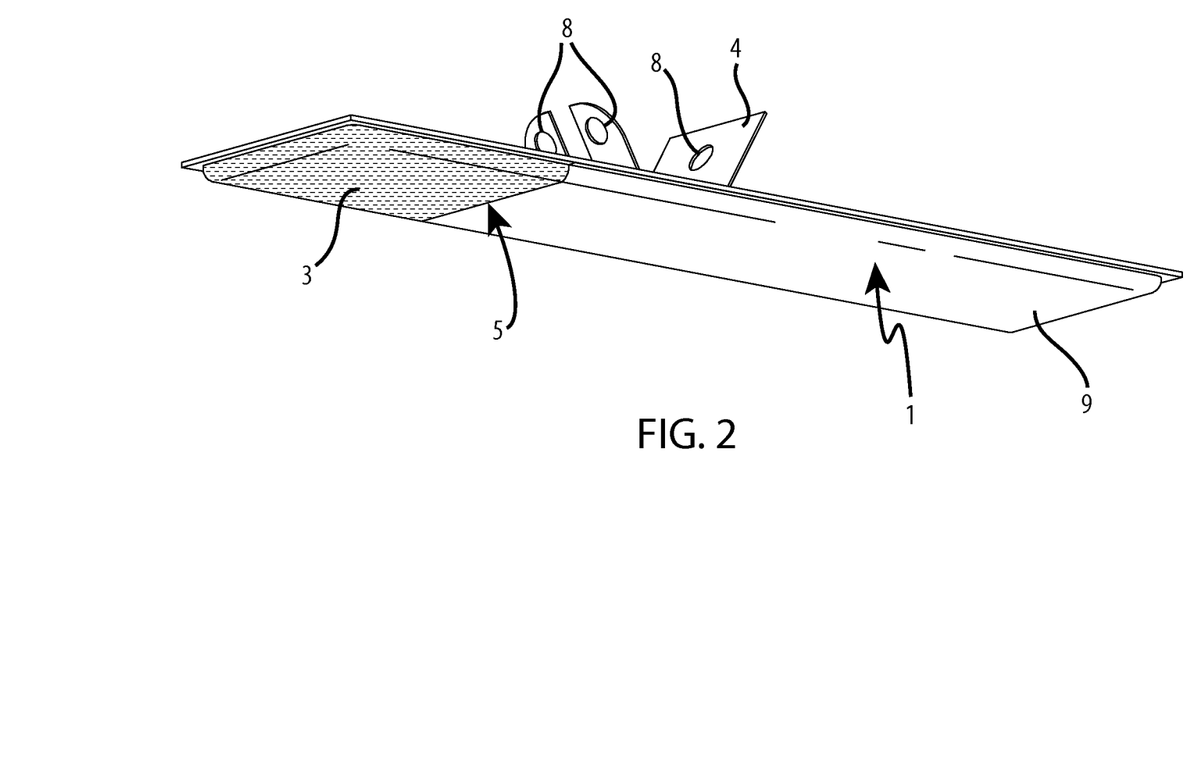
FIG. 2 depicts a single strap with padding that connects to a pump and wraps around the thigh of a user in accordance with at least one embodiment described herein.

As shown in FIG. 2, for at least one embodiment a strap may be configured to include one or more layers of padding 9. It is to be appreciated that the straps illustrated in FIG. 2 may be the same as or different from the straps shown in FIG. 1. The one or more layers of padding 9 may be provided to increase a perceived level of comfort of a user of the straps and embodiments disclosed herein. The amount of padding desired by any given user may vary and, in accordance with at least one embodiment, the strap 1 may be configured to facilitate the use of more, less or no padding. Such facilitation of the use of padding may be accomplished by providing one or more pockets in the straps in which such padding may be inserted or removed. Alternatively, straps may be configured with a pre-set level of padding or no padding, as desired by a particular user. The padding may be located, for example, on the bottom side of the strap 1 and may be configured to be proximate to and/or opposite to one or more nerve pathways in a user's inner thighs. The padding may be provided below a surface of any fastening material, such as the above described hook and loop fasteners. The one or more pads may be of varying lengths and widths. The one or more pads may be disposable, washable, recyclable, and/or configured for permanent, repetitive, single or other use. For at least one embodiment, the straps illustrated in FIG. 2 may be used and operated in the same manner as the straps illustrated in FIG. 1.

In accordance with at least one embodiment, FIGS. 3, 4, 5, and 6 illustrate an implementation where the straps serve the dual functions of (1) wrapping around the thighs and securing a pump thereto for activation and use by the user, and (2) unfolding into a deployed configuration that forms a container for storage and/or carrying of a breast pump and related accessories.

Figure 3:
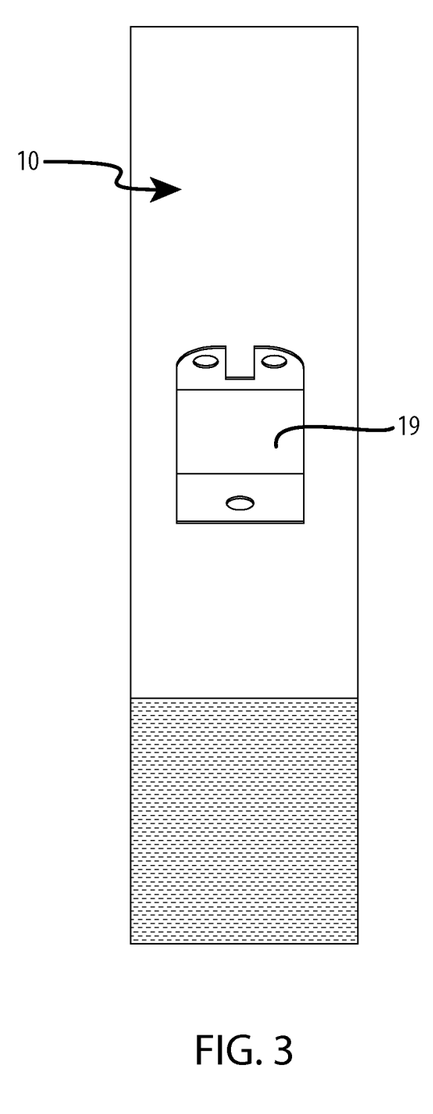
FIG. 3 depicts multiple straps folded into a single strap configuration in accordance with at least one embodiment described herein.

As shown in FIGS. 3-6, for at least one embodiment, a strap 10 may include four strap portions (as shown for example in FIG. 4) that are suitably connected and may be folded upon each other to form a single strap (as shown in FIG. 3). For example, four strap components may be stitched together such that all four straps fold together into a single strap which is 35 inches long and 2 inches wide. When configured into a single strap arrangement, each of the straps may be secured in place by the use of one or more of the before mentioned fasteners.

Figure 4:
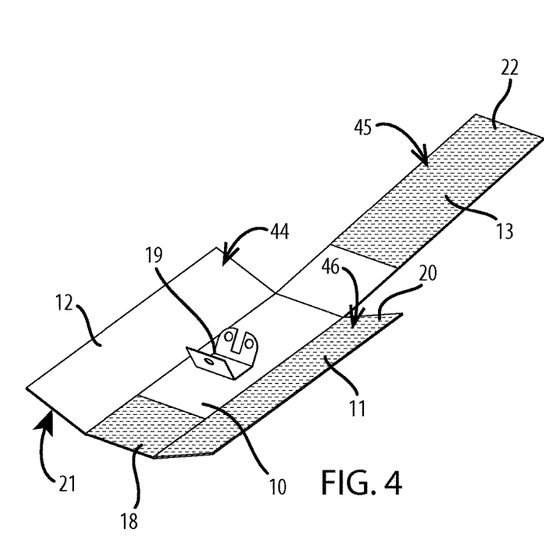
FIG. 4 depicts the multiple straps embodiment depicted in FIG. 3 in an unfolded configuration in accordance with at least one embodiment described herein.

As shown in FIG. 4 and in accordance with at least one embodiment of a left leg strap the strap 10 may be unfolded into a deployed configuration, as shown by directional arrows 44, 45 and 46. As deployed, strap 10 is connected to straps 11, 12 and 13. Each of these straps is described further below.

In at least one embodiment, a top side of strap 10 in FIG. 4 may be configured to be exactly the same as the top side of strap 1. A bottom side of strap 10 may similarly be configured to include hook and loop fasteners 18. Such hook and loop fasteners may extend, for example, 33 inches from the opposite end from where strap 13 is stitched to strap 10. Strap 10 may also include a pump connector 19. Pump connector 19 may be exactly the same as or different from pump connector 4 as preferred for any given implementation of one or more of the disclosed embodiments.

Strap 11 as illustrated in FIG. 4 may be configured to be, for example, the same length as strap 10 or otherwise. In at least one embodiment, strap 11 is the same length as strap 10, which as described above for one embodiment is 35 inches long and 2 inches wide. Strap 11 may be connected to strap 10 using any known techniques. For example, strap 11 may be stitched to strap 10 along an edge of strap 10 and a corresponding edge of strap 11. In at least one embodiment, strap 11 and strap 10 may be configured from a contiguous piece of material or otherwise.

Strap 11 may be configured to include hook and loop fasteners 20 stitched on all or a portion of the top side. Strap 12 as illustrated in FIG. 4 is 35 inches long and 2 inches wide. Strap 12 may be stitched to strap 10 along the 35 inch long edge that is opposite from the 35 inch long edge connected to strap 11. For at least one embodiment, strap 12 may be configured from a contiguous piece of material. Strap 12 may be configured to include hook and loop fasteners 21 stitched on all or a portion of the bottom side. Strap 13 may be stitched to strap 10 along a 2 inch edge. For at least one embodiment, strap 13 may be configured from a contiguous piece of material. Strap 13 may be configured to include hook and loop fasteners 22 on all or a portion of the top side extending 33 inches from the opposite end from where strap 13 is stitched to strap 10.

Figure 5:
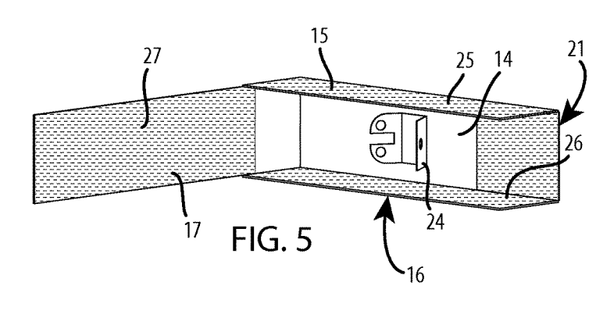
FIG. 5 depicts the multiple straps embodiment depicted in FIGS. 3 and 4 in an unfolded configuration and wherein the multiple straps connect to form a case in accordance with at least one embodiment described herein.

FIG. 5 illustrates an unfolded version of FIG. 3 for the user's right leg. For at least one embodiment, the top side of strap 14 on FIG. 5 is configured to be the same size and configuration as the top side of strap 1. It is to be appreciated however that some variance in length, width and thicknesses may be tolerated. Desirably, such variances are less than ¼ of an inch in any dimension. The bottom side of strap 14 may be configured to include hook and loop fasteners extending 33 inches from the opposite end from where strap 17 is stitched to strap 14. Strap 14 may be configured for at least one embodiment to include a pump connector 24 that uses the same shape, size and material as pump connector 4. Again, it is to be appreciated that manufacturing variances may occur, but, generally such variances should be of less than ¼ inch in any given dimension. Further, it is to be appreciated that a pump connector used in any given embodiment may vary by which leg is used to secure the pump and the characteristics of a given pump to be secured.

As shown for at least one embodiment, strap 15 as illustrated in FIG. 5 may be configured to be 35 inches long and 2 inches wide. Strap 15 may be stitched to strap 14 along a 35 inch long edge. Strap 15 may include hook and loop fasteners 25 stitched on all or a portion of the bottom side. Strap 16 as illustrated in FIG. 5 may be configured to be 35 inches long and 2 inches wide. Strap 16 may be stitched to strap 14 along the 35 inch long edge that is opposite from the 35 inch long edge connected to strap 15. Strap 16 may be configured to include hook and loop fasteners 26 stitched on all or a portion of the top side. Strap 17 may be stitched to strap 14 along a 2 inch edge. Strap 17 may include hook and loop fasteners 27 on the top side extending 33 inches from the opposite end from where strap 17 is stitched to strap 14.

Figure 6:
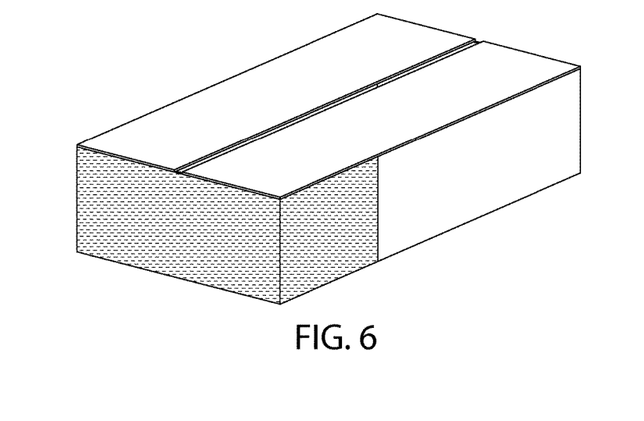
FIG. 6 depicts one half of the case as configured from the unfolded straps from FIG. 4 and in accordance with at least one embodiment described herein.

To assemble the carrying case, the user places each strap 10 on a flat surface, such as a counter with the top side facing up. The user then places the breast cups, hoses, and milk containers on strap 10. The user then folds straps 11 and 12 upwards. The user then attaches strap 11 to strap 15 by attaching the hook and loop fasteners 20 on the top of strap 11 to the hook and loop fasteners 25 on the bottom of strap 15. The user then attaches strap 12 to strap 16 by attaching the hook and loop fasteners 21 on the bottom of strap 12 to the hook and loop fasteners 26 on the top of strap 16. The user then attaches strap 13 to strap 14 by attaching the hook and loop fasteners 22 on the top of strap 13 to the hook and loop fasteners 23 on the bottom of strap 14. Finally, the user attaches strap 17 to strap 10 by attaching the hook and loop fasteners 27 on the top of strap 17 to the hook and loop fasteners 18 on the bottom of strap 10. FIG. 6 illustrates the carrying case completely assembled.

It is to be appreciated that a single strap may also be configured to function as a storage/carrying case for at least one embodiment. In accordance with such embodiment, an additional piece of strap material (not shown) having hook and loop materials in opposing positions, may be used to close or seal any openings that otherwise arise with the use of just the single strap.

While various embodiments of the invention have been described above, it should be understood that they have been presented by way of example only, and not limitation. For example, the straps described herein can include various combinations and/or sub-combinations of the components and/or features of the different embodiments described. Although described with reference to use with a breast pump, it should be understood that the straps described herein, as well as the methods of using such straps can be used with other devices and systems.

The invention claimed is:

1. A strap apparatus for use in securing at least one end of a breast pump comprising:
   a strap having a first portion proximate to a first end, a middle portion, a second portion proximate to a second end, a top side, a bottom side, a length, a width and a thickness; wherein the first portion overlaps the second portion of the strap such that the strap is configurable to wrap around a user's leg;
   at least one first fastener on the first portion, wherein each of the at least one first fastener secures the first portion of the strap to the second portion such that the strap is configurable to wrap around the user's leg; and
   a pump connector; wherein the pump connector is positioned in the middle portion on the top side of the strap, wherein the pump connector comprises at least one hole that passes through a surface making up a portion of the pump connector; wherein the at least one hole accommodates at least one hose of a breast pump; and whereby the at least one hose, upon being inserted into the at least one hole, secures the breast pump to the strap.

2. The strap apparatus of claim 1, comprising:
   at least one pad on the bottom side of the strap.

3. The strap apparatus of claim 1, comprising:
   at least one second fastener on the second portion.

4. The strap apparatus of claim 3, wherein the at least one first fastener and the at least one second fastener comprise hook and loop fastener materials.

5. The strap apparatus of claim 4, wherein the at least one first fastener is hook fastener material.

6. The strap apparatus of claim 5, comprising at least one pad on the bottom side of the strap.

7. The strap apparatus of claim 3, wherein the first fastener and the second fastener are at least two opposing snaps.

8. The strap apparatus of claim 7, wherein the at least two opposing snaps are spaced evenly along the length of the strap.

9. The strap apparatus of claim 7, wherein the at least two opposing snaps are spaced evenly along the width of the strap in each of the first portion and the second portion.

10. The strap apparatus of claim 1, further comprising a breast pump having a hose, wherein the breast pump and hose are connected to the pump connector and extend therefrom such that the breast pump can be operated between a user's thighs.

11. The strap apparatus of claim 10, wherein the breast pump is manually operated.

12. The strap apparatus of claim 10, wherein the hose is passed through a hole on the surface of the connecter so the hose operably extends to a breast cup.

13. The strap apparatus of claim 1, wherein one first fastener secures the first portion of the strap to the second portion such that the strap is configurable to wrap around the user's leg by overlapping the first portion and the second portion to form an overlapping section and the pump connector is positioned in the middle portion such that the pump connector is not overlapped.

14. A strap apparatus for use in securing at least one end of a breast pump comprising:
   a strap having a first portion proximate to a first end, a middle portion, a second portion proximate to a second end, a top side, a bottom side, a length, a width and a thickness; wherein the first portion overlaps the second portion of the strap such that the strap is configurable to wrap around a user's leg;
   at least one first fastener on the first portion, wherein each of the at least one first fastener secures the first portion of the strap to the second portion such that the strap is configurable to wrap around the user's leg;
   a pump connector; wherein the pump connector is positioned in the middle portion on the top side of the strap; and
   a hose that, along with the breast pump, is connected to the pump connector and extends therefrom such that the breast pump can be operated between a user's thighs.

15. The strap apparatus of claim 14, comprising:
   at least one pad on the bottom side of the strap and at least one second fastener on the second portion.

16. The strap apparatus of claim 15, wherein the at least one first fastener and the at least one second fastener comprise hook and loop fastener materials with the at least one first fastener being hook fastener material.

17. The strap apparatus of claim 15, wherein the first fastener and the second fastener are at least two opposing snaps spaced evenly along the length of the strap in each of the first portion and the second portion.

18. The strap apparatus of claim 14, wherein the breast pump is manually operated.

19. The strap apparatus of claim 14, wherein the hose is passed through a hole on a surface of the pump connector so the hose operably extends to a breast cup.

20. The strap apparatus of claim 14, wherein one first fastener secures the first portion of the strap to the second portion when the strap is wrapped around the user's leg by overlapping the first portion and the second portion to form an overlapping section and the pump connector is positioned in the middle portion such that the pump connector is not overlapped.

* * * * *